United States Patent [19]
Kirkpatrick

[11] 4,066,436
[45] Jan. 3, 1978

[54] METHOD OF CONTROLLING SICKLEPOD IN SOYBEANS

[75] Inventor: Joel L. Kirkpatrick, Overland Park, Kans.

[73] Assignee: Gulf Oil Corporation, Pittsburgh, Pa.

[21] Appl. No.: 701,264

[22] Filed: June 30, 1976

[51] Int. Cl.$^2$ .............................................. A01N 9/12
[52] U.S. Cl. .................................... 71/90; 260/302 D
[58] Field of Search .............................................. 71/90

[56] References Cited
U.S. PATENT DOCUMENTS 3,726,892  4/1973  Cebalo .................................... 71/90

FOREIGN PATENT DOCUMENTS 1,816,568  11/1970  Germany ................................. 71/90

OTHER PUBLICATIONS

Metzger et al. "Herbicidal 1,3,4-thiadiazolylureas" (1974) CA 82 No. 57702c, (1975).

Primary Examiner—Glennon H. Hollrah
Attorney, Agent, or Firm—Carl A. Cline

[57] ABSTRACT

Broadleaf weeds, including sicklepod are selectively controlled in soybean fields by applying post-emergently to the plant foliage one of a restricted class of 5-chlorobenzylthio-1,3,4-thiadiazolylurea compounds, for example, 1,1,3-trimethyl-3-(5-p-chlorobenzylthio-1,3,4-thiadiazol-2-yl)urea.

3 Claims, No Drawings

METHOD OF CONTROLLING SICKLEPOD IN SOYBEANS

DESCRIPTION OF THE INVENTION

A. Background of the Invention

In the present state of the art of soybean culture in the United States it has become common practice to employ one of two or three available pre-emergent herbicides for weed control. In general this method gives relatively good control of grassy weeds. However, a number of broadleaf weeds benefit from the reduced competition from the grasses and create severe problems later in the growing season, sometimes sufficient to prevent the harvesting of the soybeans.

Although more effective, broader spectrum pre-emergent herbicides have been sought for use with soybeans, this approach to the problem has not been successful because of the sensitivity of soybeans to herbicides. An alternative method of controlling broadleaf weeds is to employ a post-emergent herbicide shortly after emergence of the weeds. This method is not yet a widely accepted practice because of a shortage of suitable herbicides. No more than two herbicides have given consistently acceptable results in the midwestern U.S. and cocklebur has only been controlled by applications that also caused substantial injury to soybeans. (See *Successful Farming* vol. 74 No. 4, page C12, February 1976.)

Just as soybeans are known to be sensitive to herbicides, peanuts are well known to be relatively insensitive, and permit the use of a much wider variety of herbicides. However, in the southeastern U.S. a herbicide-resistant weed has become a pest in peanuts in spite of the use of herbicides, probably benefiting from reduced competition. This weed, commonly called sicklepod has spread widely and is now probably the worst weed in soybeans in southeastern U.S. (See *Weeds Today*, Spring 1976, pages 12–14.) This weed problem is being attacked by means of mechanical cultivation and a variety of both pre-emergent and post-emergent herbicides. However, erratic results have been obtained with herbicides under the various soil and climatic conditions which exist in the area.

B. Summary of the Invention

I have discovered that broadleaf weeds including sicklepod can be selectively controlled in soybean fields by applying post-emergently an effective amount, sufficient to kill weeds but insufficient to cause substantial permanent injury to soybeans, of a compound having the general structural formula:

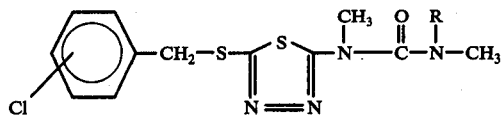

in which R represents hydrogen or a methyl substituent with the additional provision that when the chloro substituent is in the para position on the benzyl structure, R is methyl. In general, compounds with substituents in the meta position exhibit greater herbicidal activity and are preferred for that reason.

C. DETAILED DESCRIPTION (1) Synthesis of the Herbicides

The general method of synthesis of the herbicides employed in the method of this invention is outlined below:

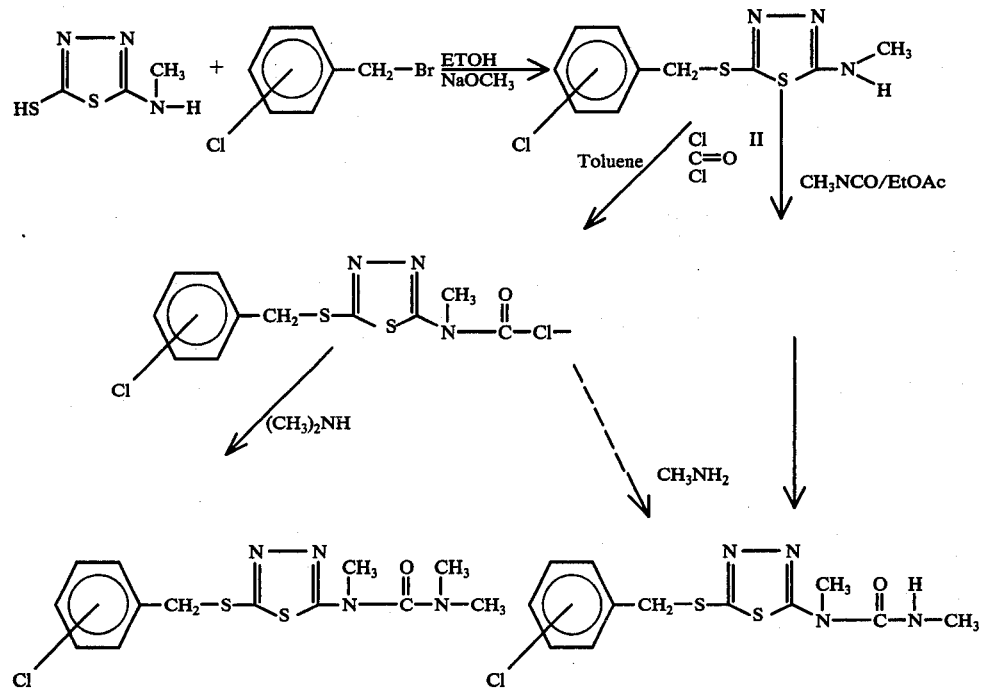

The following procedures, directed to the synthesis of unsubstituted benzyl compounds, are presented for purposes of illustration of a suitable general method of preparing compounds of the type employed in the method of the invention, using known compounds as starting materials.

Preparation of 2-methylamino-5-benzylthio-1,3,4-thiadiazole

To a solution of sodium ethoxide in ethanol (prepared by adding 13.5 g of anhydrous sodium methoxide to 300 ml of absolute ethanol) was added 31 g of 2-methylamino-5-mercapto-1,3,4-thiadiazole. After stirring for 15 min. at room temperature, 36 g of benzyl bromide was added to the homogeneous solution and the reaction heated to reflux for 4 hrs. At the end of the reflux period, most of the ethanol was removed at reduced pressure, water was added and the reaction extracted with ethyl acetate, which was washed with water and saturated NaCl, then dried over $Na_2SO_4$. Removal of the solvent gave a viscous oil which was crystallized from a mixture of ether and petroleum ether to give 29.7 g of 2-methylamino-5-benzylthio-1,3,4-thiadiazole, MP 87–89¼C.

Preparation of 1,1,3-Trimethyl-3-(5-benzylthio-1,3,4-thiadiazol-2-yl)urea

A slurry of 10 g of 2-methylamino-5-benzylthio-1,3,4-thiadiazole in toluene (150 ml) was saturated with anhydrous HCl at 0°, then phosgene was bubbled through the mixture at a moderate rate while gradually increasing the temperature to reflux. After a few minutes at reflux temperature, the reaction became homogeneous and the phosgene flow discontinued, substituted by an argon flow to remove excess phosgene. The solution was cooled to room temperature and treated with an excess of 40% dimethyl amine. After stirring at room temperature for 30 min. the toluene was washed with 10% hydrochloric acid, water, saturated NaCl, and dried over $Na_2SO_4$. Removal of the solvent at reduced pressure gave a heavy oil which was crystallized from ether-petroleum ether. The product 1,1,3-trimethyl-3-(5-benzylthio-1,3,4-thiadiazol-2-yl)urea was collected, wt. 12.5 g, MP 48°–51° C.

Preparation of 1,3-Dimethyl-3-(5-benzylthio-1,3,4-thiadiazol-2-yl)urea

To a solution of 2-methylamino-5-benzylthio-1,3,4-thiadiazole (4.0 g) in ethyl acetate (100 ml) was added 1.5 g of methyl isocyanate. The reaction was stirred at room temperature for 2 hrs then heated at reflux for an additional 2 hrs. The product, 1,3-dimethyl-3-(5-benzylthio-1,3,4-thiadiazol-2-yl)urea, crystallized upon the addition of petroleum ether, was collected, washed with ether and dried to give 4.7 g, MP 139°–142° C.

In the following table are listed compounds which have been made by means of procedures of the type illustrated above.

TABLE 1

Compounds of the formula

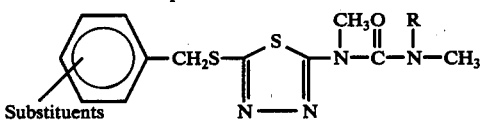

| Compound No. | R | Substituents on benzyl structure | m.p. (° C.) |
|---|---|---|---|
| 1 | H | m-chloro | 118–120 |
| 2 | methyl | p-chloro | 84–86 |
| 3 | H | p-nitro | 168–171 |
| 4 | H | 2,6-dichloro | 210–213 |
| 5 | H | 3,4-dichloro | 118–120 |
| 6 | H | p-chloro | 139–141 |

Compounds numbered 3, 4, 5 and 6 above are unsuitable for use in the present invention and are only included to demonstrate the narrow limits of suitability. Compound No. 3 is not sufficiently effective against such weeds as pigweed, velvet leaf and morning glory, for example, when applied at rates low enough to avoid substantial permanent injury to soybeans. Compounds numbered 5 and 6 also fail to produce total kills of sicklepod and other weeds when applied at rates low enough to avoid substantial permanent injury to soybeans. Compound No. 4 has so little phytotoxicity of any kind that it appears to have no practical utility as an agricultural herbicide.

(2) Weed Control in Presence of Soybeans

Post-emergent control of weeds in the presence of soybeans may be demonstrated in the greenhouse by means of the procedure outlined below.

PROCEDURE

Greenhouse potting soil is placed in rectangular trays, commonly called "flats" made of expanded polystyrene and measuring about 12 in. by 6 in. by 3 in. in depth. Seeds of the test species are planted in the soil and the planted flats are placed on the greenhouse benches where temperature and watering are regulated to provide good growth conditions. At about 13 days after planting when all plants have emerged and have exhibited normal growth, the plants are sprayed with an aqueous dispersion of herbicide at a spray volume of 40 ga./A. Spray mixtures may be made conveniently by diluting with water an emulsifiable concentrate containing, besides the herbicide, a solvent such as a mixture of three parts xylene and one part isophorone, along with about one part of a commercial emulsifier consisting of a blend of anionic and nonionic surface active agents.

At 2 to 3 weeks after spraying the condition of the plants is observed and is rated on a scale of 1 to 10, ranging from observable temporary injury to total kill. Where no injury is observable, the rating is zero. Representative results are presented for illustrative purposes in the following table. Where two scores appear, they represent results of separate tests, one conducted early in the year and one in late spring or early summer.

TABLE 2

Results of Greenhouse Tests

| Species | Appl. Rate oz./A. | Scores for Compounds Compound No. 1 | Compound No. 2 |
|---|---|---|---|
| Pigweed | 8 | 10 | |
| | 4 | 10 | |
| | 2 | 10 | |
| | 1 | 4 | |
| Smartweed | 8 | 10 | |
| | 4 | 10 | |
| | 2 | 10 | |
| | 1 | 10 | |
| Velvet leaf | 8 | 10 | |
| | 4 | 10 | |
| | 2 | 10 | |
| | 1 | 6 | |
| Jimson weed | 8 | 10 | |
| | 4 | 10 | |
| | 2 | 10 | |
| | 1 | 10 | |
| Morning glory | 8 | 10 | |
| | 4 | 10 | |
| | 2 | 10 | |
| | 1 | 5 | |
| Cocklebur | 8 | 10 | |
| | 4 | 10 | |
| | 2 | 10 | |
| | 1 | 5 | |
| Beggarweed | 8 | 10 | 10 |
| | 4 | 10 | 10 |

TABLE 2-continued
Results of Greenhouse Tests

| Species | Appl. Rate oz./A. | Scores for Compounds Compound No. 1 | Compound No. 2 |
|---|---|---|---|
| | 2 | 10 | 10 |
| | 1 | 10 | 10 |
| Sesbania | 8 | 10 | 10 |
| | 4 | 10 | 10 |
| | 2 | 10 | 10 |
| | 1 | 10 | 5 |
| Sicklepod | 8 | 10 | 10 |
| | 4 | 10 | 10 |
| | 2 | 10 | 10 |
| | 1 | 10 | 10 |
| Prickly sida | 8 | 10 | 10 |
| | 4 | 10 | 10 |
| | 2 | 10 | 10 |
| | 1 | 6 | 8 |
| Soybeans | 8 | 3, 2 | 3 |
| | 4 | 1, 2 | 1 |
| | 2 | 1, 1 | 1 |
| | 1 | 0, 0 | 0 |

The amount of herbicide which is effective against plants grown under excellent conditions may be judged by examination of the data presented above. It is understood by those skilled in the art that plants grown under adverse conditions may require more herbicide. It is also a common practice to use less efficient methods of application to prevent spray from drifting in the wind. Allowance must therefore be made according to conventional practice, for spray that does not reach the foliage, but falls on the ground and is wasted. Because of the high degree of efficacy of the compounds employed in the method of the invention, it is preferred to apply the compounds in inert diluents so as to obtain more even distribution. Water and inert powdered solids are preferred as diluents, according to conventional practice.

I claim:

1. The method of selectively controlling broadleaf weeds in soybean fields comprising applying post-emergently to the plants in said fields an effective amount sufficient to kill weeds, including sicklepod but insufficient to cause substantial permanent injury to soybeans, of a compound having the general structural formula

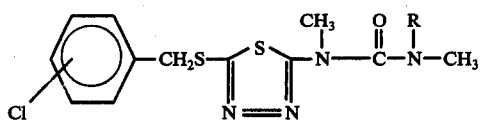

in which R is hydrogen or methyl, with the additional provision that when the chloro substituent is in the para position on the benzyl structure, R is methyl.

2. The method of selectively controlling broadleaf weeds in soybean fields comprising applying post-emergently to the plants in said fields an effective amount, sufficient to kill weeds, including sicklepod, but insufficient to cause substantial permanent injury to soybeans, of a compound having the structural formula

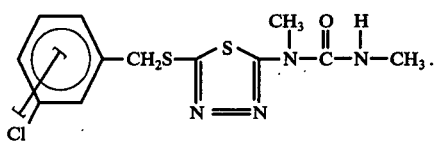

3. The method of selectively combating weeds in soybean fields comprising applying post-emergently to the plants in said fields an effective amount, sufficient to kill weeds, including sicklepod, but insufficient to cause substantial permanent injury to soybeans, of a compound having the structural formula

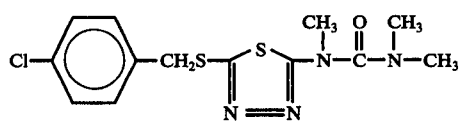

* * * * *

UNITED STATES PATENT OFFICE
CERTIFICATE OF CORRECTION

Patent No. 4,066,436                    Dated January 3, 1978

Inventor(s) Joel L. Kirkpatrick

It is certified that error appears in the above-identified patent and that said Letters Patent are hereby corrected as shown below:

Column 2, line 15, the general structural formula should be:

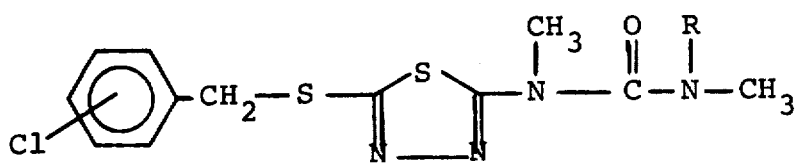

Column 6, line 5, the general structural formula should be:

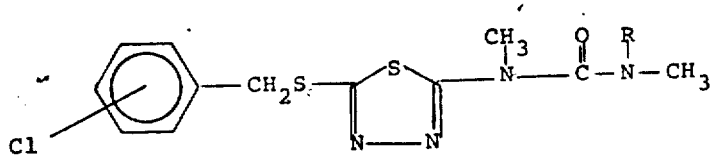

Column 6, line 20, the general structural formula should be:

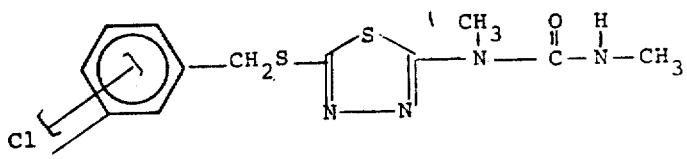

UNITED STATES PATENT OFFICE
CERTIFICATE OF CORRECTION

Patent No. 4,066,436  Dated January 3, 1978

Inventor(s) Joel L. Kirkpatrick

It is certified that error appears in the above-identified patent and that said Letters Patent are hereby corrected as shown below:

Column 6, line 35, the general structural formula should be:

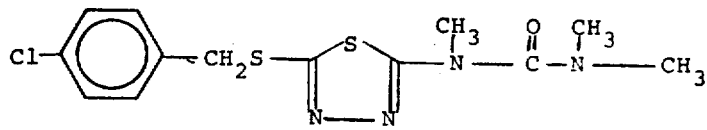

Signed and Sealed this

Thirtieth Day of May 1978

[SEAL]

Attest:

RUTH C. MASON  
Attesting Officer

LUTRELLE F. PARKER  
Acting Commissioner of Patents and Trademarks